US006965043B1

(12) United States Patent
Kenneally et al.

(10) Patent No.: US 6,965,043 B1
(45) Date of Patent: Nov. 15, 2005

(54) PROCESS FOR MAKING HIGH PURITY FATTY ACID LOWER ALKYL ESTERS

(75) Inventors: Corey James Kenneally, Mason, OH (US); Gary Allen Busch, Cincinnati, OH (US); Erich William Gansmuller, Norwood, OH (US)

(73) Assignee: Procter + Gamble Co., Cincinnati, OH (US)

(*) Notice: Subject to any disclaimer, the term of this patent is extended or adjusted under 35 U.S.C. 154(b) by 0 days.

(21) Appl. No.: 09/554,211

(22) PCT Filed: Nov. 2, 1998

(86) PCT No.: PCT/US98/23311

§ 371 (c)(1),
(2), (4) Date: May 10, 2000

(87) PCT Pub. No.: WO99/24387

PCT Pub. Date: May 20, 1999

Related U.S. Application Data

(60) Provisional application No. 60/064,782, filed on Nov. 10, 1997.

(51) Int. Cl.[7] ............................................. C07C 51/00
(52) U.S. Cl. ....................................... 554/167
(58) Field of Search .............................. 554/161, 162, 554/167, 168

(56) References Cited

U.S. PATENT DOCUMENTS

| | | | |
|---|---|---|---|
| 2,383,579 A | 8/1945 | Allen et al. | |
| 2,383,580 A | 8/1945 | Arrowsmith et al. | |
| 2,383,596 A | 8/1945 | Dreger et al. | |
| 2,383,599 A | 8/1945 | Glossop | |
| 2,383,601 A | 8/1945 | Kelm ....................... | 260/410.9 |
| 2,383,602 A | 8/1945 | Keim et al. | |
| 2,383,614 A | 8/1945 | Percy | |
| 2,383,632 A | 8/1945 | Trent | |
| 2,383,633 A | 8/1945 | Trent | |
| 3,600,186 A | 8/1971 | Mattson et al. | |
| 3,963,399 A | 6/1976 | Zavasnik | |
| 3,963,699 A | 6/1976 | Rizzi et al. | |
| 4,005,195 A | 1/1977 | Jandacek | |
| 4,005,196 A | 1/1977 | Jandacek et al. | |
| 4,517,360 A | 5/1985 | Volpenhein | |
| 4,518,772 A | 5/1985 | Volpenhein | |
| 4,668,439 A | 5/1987 | Billenstein et al. ...... | 260/410.9 |
| 4,806,632 A | 2/1989 | McCoy et al. | |
| 4,931,552 A | 6/1990 | Gibson et al. | |
| 5,116,546 A * | 5/1992 | Klok et al. .................. | 554/167 |
| 5,273,772 A | 12/1993 | Cooper | |
| 5,288,884 A | 2/1994 | Cooper | |
| 5,298,637 A | 3/1994 | Cooper | |
| 5,362,894 A | 11/1994 | Handwerker et al. | |
| 5,374,446 A | 12/1994 | Ferenz et al. | |
| 5,387,429 A | 2/1995 | Cooper | |
| 5,422,131 A | 6/1995 | Elsen et al. | |
| 5,427,815 A | 6/1995 | Ferenz | |
| 5,466,843 A | 11/1995 | Cooper | |
| 5,491,226 A * | 2/1996 | Kenneally .................... | 536/115 |
| 5,516,544 A | 5/1996 | Sekula et al. | |
| 5,589,217 A | 12/1996 | Mazurek | |
| 5,597,605 A | 1/1997 | Mazurek | |
| 5,767,257 A | 6/1998 | Schafermeyer et al. | |
| 5,945,529 A | 8/1999 | Corrigan et al. | |
| 6,465,642 B1 | 10/2002 | Kenneally et al. | |

FOREIGN PATENT DOCUMENTS

| | | | | |
|---|---|---|---|---|
| EP | 0 164 643 A2 | 12/1985 | | |
| EP | 391485 | * 10/1990 | | |
| EP | 391485 A1 | * 10/1990 | ........... | C07C 67/03 |
| WO | WO 94/17027 | 8/1994 | ........... | C07C 67/03 |
| WO | WO 97/27275 | 7/1997 | ........... | C11C 3/10 |

OTHER PUBLICATIONS

Deuel, Harry J., Jr.—"The Lipids, Their Chemistry and Biochemistry". vol. II: Biochemistry, Digestion, Absorption, Transport and Storage; pp. 215-218. 1955 Interscience Publishers, Inc., New York, NY.

* cited by examiner

*Primary Examiner*—Deborah D. Carr
(74) *Attorney, Agent, or Firm*—Bryn T. Lorentz; Carl J. Roof; Melody A. Jones

(57) ABSTRACT

Processes for the synthesis of high purity fatty acid lower alkyl esters comprise the steps of: (a) converting a fatty acid source to a product mixture comprising lower alkyl esters and by-products; (b) water-washing the product mixture at elevated temperature and elevated pressure to remove by-products; and (c) fractionally distilling the water-washed product mixture to obtain high purity fatty acid lower alkyl esters. At least a portion of the fatty acids have from about 20 to about 24 carbon atoms. The high purity lower alkyl esters have an acid value no greater than about 1.0.

29 Claims, No Drawings

PROCESS FOR MAKING HIGH PURITY FATTY ACID LOWER ALKYL ESTERS

This application claims the benefit of Provisional No. 60/064,782, filed Nov. 10, 1997.

TECHNICAL FIELD

This invention relates to novel processes for synthesizing high purity lower alkyl esters using water-washing and fractional distillation. In particular, the invention relates to novel processes for synthesizing high purity C22 methyl esters which are colorless and which have low iodine values and low acid values. The C22 methyl esters synthesized according to the invention have low levels of glycerine and glycerides. Additionally, this invention relates to novel processes for preparing polyol fatty acid polyesters by transesterification of polyol using high purity fatty acid lower alkyl esters prepared according to the invention.

BACKGROUND ART

The food industry has recently focused attention on polyol polyesters for use as low-calorie fats in food products. Triglycerides (triacylglycerols) constitute about 90% of the total fat consumed in the average diet. One method by which the caloric value of edible fat can be lowered is to decrease the amount of triglycerides that are consumed, since the usual edible triglyceride fats are almost completely absorbed in the human system (see Lipids, 2, H. J. Deuel, Interscience Publishers, Inc., New York, 1955, page 215). Low calorie fats which can replace triglycerides are described in Mattson, et al., U.S. Pat. No. 3,600,186. Mattson, et al. disclose low calorie, fat-containing food compositions in which at least a portion of the triglyceride content is replaced with a polyol fatty acid ester having at least four fatty acid ester groups, with each fatty acid having from eight to twenty-two carbon atoms.

A number of process have been disclosed in the art for preparing highly esterified polyol fatty acid polyesters, in particular sucrose polyesters. One such process for preparing these polyesters involves a solvent-free, essentially two-step transesterification of the polyol with fatty acid esters of an easily removable lower alkyl alcohol. In the first step, a mixture of polyol, fatty acid lower alkyl esters, alkali metal fatty acid soap and a basic esterification catalyst are heated to form a melt. The amount of fatty acid lower alkyl esters is such that the melt forms primarily partial fatty acid esters of the polyol, e.g. esters in which less than about 50% of the hydroxyl groups of the polyol are esterified. In the second step, an excess of fatty acid lower alkyl esters is added to the melt which is then heated to convert the partial polyol polyesters to more highly esterified polyol polyesters, e.g. those in which more than 50% of the hydroxyl groups of the polyol are esterified. See, for example, Rizzi & Taylor, U.S. Pat. No. 3,963,399, and Volpenhein, U.S. Pat. No. 4,517,360 and U.S. Pat. No. 4,512,772.

The lower alkyl esters which are used to prepare the polyol polyesters can be prepared by the transesterification of fatty acid sources such as triglyceride oils and fats with a lower alkyl alcohol in the presence of an alkali catalyst. After the transesterification reaction, a crude glycerine-containing layer comprising glycerine (glycerol) formed in the transesterification reaction, catalyst, soap formed by the catalyst, lower alkyl esters and lower alkyl alcohol, is separated from the fatty acid lower alkyl ester layer. The fatty acid lower alkyl ester layer is then purified by any suitable recovery method, such as, e.g., distillation. Processes of this type have been described in U.S. Pat. Nos. 2,383,579, 2,383,580, 2,383,596, 2,383,599, 2,383,601, 2,383,602, 2,383,614, 2,383,632 and 2,383,633, and in the European Patent No. 0 164 643. An extra esterification step before recovery, but after separation of the fatty acid lower alkyl ester layer from the glycerol layer, may also be used to produce high yields of high purity fatty acid lower alkyl esters. See European Patent No. 391 485.

Unfortunately, the lower alkyl esters prepared by any of these known processes are likely to contain some residual level of fat sources such as glycerine, and mono-, di-, or triglyceride. When these lower alkyl esters are then used to prepare polyol fatty acid polyesters, they will cause the polyol polyester product to contain undesirably high levels of triglyceride fat. These triglycerides add calories to the polyol polyesters and keep the polyol polyesters from being completely fat free.

Another disadvantage with known processes for preparing methyl esters is that fatty acid methyl esters with differing lengths of fatty acid chains are not separated from one another. As unsaturated C18 fatty acid esters are particularly suitable for making liquid polyol fatty acid polyesters, while C22 fatty acid esters are particularly suitable for making solid polyol fatty acid polyesters, it would be desirable to separate the fatty acid lower alkyl esters into fractions of specific fatty acid chain lengths.

Another disadvantage with known processes for preparing fatty acid lower alkyl esters is that during distillation undesirably high levels of free fatty acids can be formed, causing the fatty acid lower alkyl esters to have undesirably high acid values (greater than 1.0). This is particularly problematic when distilling fatty acid lower alkyl esters having long chain fatty acid moieties (fatty acid chains of 16 or more carbon atoms). Since the boiling point of a fatty acid lower alkyl ester tends to increase as the fatty acid chain length increases, the distillation temperature generally must also increase accordingly; unfortunately, higher acid values tend to be generated at higher temperatures. Therefore, the longer the fatty acid chain length, the more free fatty acids are likely to be formed during the distillation. Consequently, as the fatty acid chain length increases it becomes increasingly difficult to make fatty acid lower alkyl esters having low acid values (no greater than about 1.0).

Thus, many prior art methods which produce fatty acid lower alkyl esters are limited in that significant levels of glycerine and mono-, di- or triglycerides are contained in the esters whereby the product is not completely fat free. Additionally, many prior art methods are limited in that there is no fractionation between fatty acid lower alkyl esters with varying fatty acid chain lengths. Prior art methods are also limited in that the fatty acid lower alkyl esters generally have high acid values.

SUMMARY OF INVENTION

It is an object of this invention to obviate various problems of the prior art.

It is another object of this invention to provide novel processes for the production of high purity lower alkyl esters, especially high purity lower alkyl esters for use in polyol fatty acid polyester synthesis.

It is yet another object of this invention to provide novel processes for making high purity lower alkyl esters, which processes minimize the amount of glycerine or glyceride remaining in the alkyl ester product.

It is also an object of this invention to provide novel processes for producing fatty acid lower alkyl esters wherein esters of differing chain length are separated from one another.

It is another object of this invention to provide novel processes for the synthesis of polyol fatty acid polyesters through the transesterification of high purity fatty acid lower alkyl esters and polyol.

It is yet another object of the invention to provide novel processes for the synthesis of fatty acid lower alkyl esters having an acid value of no greater than about 1.0.

In accordance with one aspect, the present invention is directed to processes for the synthesis of high purity fatty acid lower alkyl esters. The processes comprise the steps of converting a source of fatty acids to a product mixture comprising lower alkyl esters and by-products, and water-washing the product mixture at an elevated temperature and an elevated pressures to remove by-products from the product mixture. High purity fatty acid lower alkyl esters of varying fatty acid chain length can then be separated by subjecting the water-washed product mixture to fractional distillation. Preferably, the fatty acids have from about 20 to about 24 carbon atoms and the fatty acid lower alkyl esters have an acid value no greater than about 1.0.

In accordance with another aspect, the present invention is directed to processes for the synthesis of high purity fatty acid lower alkyl esters comprising the steps of converting a source of fatty acids to a product mixture comprising fatty acid lower alkyl esters and by-products; water-washing the product mixture to remove at least a portion of the by-products, and fractionally distilling the water-washed product mixture to obtain high purity fatty acid lower alkyl esters. In order to avoid generation of high acid values the fractional distillation is performed at a low temperature in the absence of base, or at a high temperature in the presence of base. The fatty acids have at least about 16 carbon atoms, and the fatty acid lower alkyl esters have an acid value of no greater than about 1.0.

In accordance with another aspect, the present invention is directed to processes for preparing high purity fatty acid lower alkyl esters comprising the steps of reacting a fatty acid glycerol ester with a lower alkyl alcohol in the presence of a catalyst to produce a product mixture of fatty acid lower alkyl esters, fatty acid glycerol esters and glycerol; separating the product mixture into a glycerol-containing phase and a fatty acid lower alkyl ester-containing phase; water-washing the fatty acid lower alkyl ester-containing phase at elevated temperatures and elevated pressures; and subjecting the resulting water-washed lower alkyl esters to fractional distillation. The high purity fatty acid lower alkyl esters generally have an acid value of no greater than about 1.0, preferably less that about 1.0, and more preferably less than about 0.5.

In accordance with another aspect, the present invention relates to processes for the preparation of polyol fatty acid polyester using high purity lower alkyl esters, which processes comprise the step of transesterifying a polyol with the high purity fatty acid lower alkyl ester.

In accordance with yet another aspect, the present invention relates to processes for the preparation of linked esterified alkoxylated polyols, preferably high molecular weight linked esterified propoxylated glycerines, using high purity lower alkyl esters, which processes comprise the step of transesterification of a linked alkoxylated polyol with the high purity fatty acid lower alkyl ester.

It has been found that high purity fatty acid lower alkyl esters of specific chain lengths can be obtained through the use of high temperature-high pressure water washing and fractional distillation. Such high purity lower alkyl esters are advantageously suited for use in polyol fatty acid polyester synthesis. Particularly, the present invention relates to processes for the synthesis of high purity behenic acid methyl esters. Such high purity behenic acid esters have low iodine values (about 2 or less) and low acid values (preferably less that about 1.0, and more preferably less than about 0.5).

These and additional objects and advantages will be more fully apparent in view of the following detailed description.

DETAILED DESCRIPTION OF THE INVENTION

The present invention encompasses processes for synthesizing high purity lower alkyl esters from fatty acid sources. Such high purity lower alkyl esters have high levels of functional saturates, low acid values, colorless appearance, and low levels of glycerine (glycerol) and glycerides (glycerol esters). As used herein, the term "lower alkyl ester" is intended to include fatty acid esters of lower alkyl alcohols, in which the hydroxyl groups are replaced with esters of fatty acids. Suitable lower alkyl alcohols include mono-alcohols having from about 1 to about 6 carbon atoms. Especially preferred lower alkyl esters are methyl esters. As used herein, the term "high purity" is intended to mean the level of fatty acid lower alkyl esters is at least about 85%, by weight, preferably about 90%, by weight. The high purity fatty acid lower alkyl esters preferably have at least about 16 carbon atoms in the fatty acid moiety, more preferably from about 16 to about 24 carbons atoms, even more preferably from about 20 to about 24 carbon atoms, and most preferably from about 22 to about 24 carbon atoms.

To obtain lower alkyl esters, a fatty acid source, such as fatty acid glycerol esters (mono-, di-, and triglycerides), acid chlorides, or acid anhydrides, is converted to fatty acid lower alkyl esters. Fatty acid lower alkyl esters can be prepared by reacting fatty acid glycerol esters with a monohydric alcohol, preferably in the presence of a suitable catalyst, to produce a product mixture comprising fatty acid lower alkyl esters, unreacted or partially reacted fatty acid glycerol esters (glycerides), glycerol, catalyst, soap, and lower alkyl alcohol according to the method described in Kenneally, U.S. Pat. No. 5,491,226, incorporated herein by reference. Suitable monohydric lower alkyl alcohols for use in preparing the lower alkyl esters used in the process of the present invention include $C_1$–$C_6$ mono-alcohols. Methanol is an especially preferred alcohol for use in the process of the present invention. Suitable fatty acid glycerol esters, which include mono-, di- and triglycerides, can be derived from either synthetic or natural, saturated or unsaturated fatty acids and include positional and geometrical isomers.

The high purity lower alkyl esters have low acid values of less than about 1.0; as used herein the term "acid value" is intended to indicate twice the level of free fatty acid in the lower alkyl ester; the acid value (AV) is equivalent to the free fatty acid value (FFA) multiplied by two (FFA×2=AV). One method of determining free fatty acid level is with phenolphthalein titration. For example, one milliliter of phenolphthalein indicator, 50±0.2 grams of sample and 100 ml of warm neutral denatured alcohol are mixed. The solution is titrated to a phenolphthalein endpoint using 0.01N NaOH. The percent free fatty acid (free fatty acid value or FFA) is reported as % oleic acid, and is calculated according to the equation:

$$FFA \text{ as } \% \text{ Oleic} = \frac{[(\text{ml of NaOH}) \times (\text{Normality of NaOH}) \times 28.21]}{\text{Sample Weight}};$$

wherein ml NaOH is the amount of NaOH required to reach the phenolphthalein titration end point, and the acid value (AV) is calculated as FFA×2=AV. Generally, the acid value of high purity lower alkyl esters according to the invention is no greater than about 1.0 (free fatty acid value no greater than about 0.5). Preferably the acid value is less than about 1.0, and more preferably is less than about 0.5, even more preferably is less than about 0.3, and most preferably is less than about 0.2.

In order to obtain low acid values, a basic catalyst, rather than an acidic catalyst, is used to form the lower alkyl esters. Suitable basic catalysts for use in preparing the lower alkyl esters include alkali metals such as sodium, lithium and potassium, alloys of two or more alkali metals, such as sodium-lithium and sodium-potassium alloys; alkali metal hydrides, such as sodium, lithium and potassium hydrides; alkali metal lower (C1–C4) alkyls such as butyl lithium; and alkali metal alkoxides of lower (C1–C4) alcohols, such as lithium methoxide, potassium t-butoxide, potassium methoxide and/or sodium methoxide. Sodium methoxide is an especially preferred catalyst.

Techniques used to achieve low acid values include maintaining the pH of the ester synthesis process above about 7, and using a base neutralization of fatty acids in the stillpot prior to completion of distillation. To minimize free fatty acid levels, the stillpot temperature is preferably less than about 274° C. (525° F.), more preferably less than about 246° C. (475° F.), and most preferably about 218° C. (425° F.); total batch residence time is preferably less than about 20 hours, more preferably less than about 10 hours, most preferably less than about 1 hour.

The reaction between the fatty acid glycerol ester and the monohydric alkyl alcohol can be carried out using conventional transesterification conditions. In general, the reaction will be carried out at elevated temperatures; the specific temperature depends on the particular blend of fatty acid residues and alcohols, and ranges from about 20° C. (68° F.) to about 160° C. (320° F.), preferably from about 30° C. (86° F.) to about 120° C. (248° F.), and more preferably from about 40° C. (104° F.) to about 80° C. (176° F.). The reaction may occur under pressures of atmospheric, as well as sub- or super-atmospheric, typically the pressure is from about atmospheric to about 150 psig. Preferably some agitation is applied to the reactants, e.g. by stirring the reaction mixture.

As used herein, all ratios are molar ratios unless otherwise specified, and all percentages are by weight unless otherwise specified. In general, the monohydric alkyl alcohol is present in a stoichiometric excess with respect to the fatty acid residues of the one or more fatty acid glycerol esters. Typically, the molar ratio of monohydric alkyl alcohol to glycerol ester fatty acid residues is greater than 3:1, preferably greater than 5:1, and more preferably greater than 6:1, even more preferably about 7.2:1. The molar ratio of catalyst to glycerol ester fatty acid residues generally ranges from about 0.002:1 to about 1:1, preferably from about 0.01:1 to about 0.1:1; more preferably from about 0.02:1 to about 0.08:1.

Using the above described transesterification conditions, suitable reaction times range from about 10 minutes to several hours, preferably from about 30 minutes to about three hours. A product mixture is obtained which comprises fatty acid lower alkyl esters and by-products.

The product mixture is then separated into a lower layer rich in glycerol and an upper layer rich in fatty acid lower alkyl ester. The separation can be accomplished by conventional means such as gravity or centrifugal force. The lower layer rich in glycerol is removed from the product mixture. The remaining product mixture comprises the upper layer rich in fatty acid lower alkyl ester. The fatty acid lower alkyl ester-containing phase of the product mixture may also contain by-products such as fatty acid glycerol esters, soap, lower alkyl alcohol, catalyst and residual glycerol. The fatty acid lower alkyl ester-containing phase of the product mixture is subjected to water washing to extract fatty acid glycerol esters, soap, lower alkyl alcohol, catalyst and residual glycerol.

Preferably, high temperature-high pressure water-washing of the fatty acid lower alkyl ester-containing product mixture is used to remove the by-products. Water-washing reduces the glycerol level in the fatty acid lower alkyl ester prior to distillation. Generally the solubility of glycerol and long chain alkali soaps (such as sodium soaps) in the water phase increases as the temperature increases, allowing for better phase separation and greater removal of glycerine. The water-washing temperature is from about 21° C. (70° F.) to about 93° C. (200° F.), preferably from about 60° C. (140° F.) to about 93° C. (200° F.), more preferably from about 77° C. (170° F.) to about 93° C. (200° F.), most preferably about 88° C. (190° F.) to about 93° C. (200° F.). To achieve effective phase separation, boiling of the water and residual lower alkyl alcohol are minimized by placing the water wash and separation vessel under slight pressure, typically 1000 mm/Hg (5 psig). Methyl esters made according to the invention generally have a level of monoglyceride below about 500 ppm, a non-detectable level of di- and triglycerides, and a glycerol level of less than about 200 ppm.

Typically from about 2% to about 50%, by weight, of the ester-containing phase of the water is added to the fatty acid lower alkyl ester-containing phase in a stirred tank, a column or an in-line static mixer for from about 0.1 minute to about 60 minutes at elevated temperatures, i.e., temperatures of from about 20° C. (68° F.) to about 90° C. (200° F.). The fatty acid lower alkyl esters are generally water-washed at temperatures slightly above their melting points; for example, low Iodine Value (IV) rapeseed methyl esters (melting point approximately 58° C. (136° F.) are generally water-washed at temperatures of from about 60° C. (140° F.) to about 90° C. (194° F.). The water washing is generally done at elevated pressures; i.e., at atmospheric or super-atmospheric pressures (pressures of about 760 mm of mercury or greater). Typically, the pressure is increased as necessary to suppress boiling of the water and residual lower alkyl alcohols. Generally, pressures of from about 760 mm Hg (0 psig) to about 1000 mm Hg (about 5 psig) are used; preferably the pressure is about 1000 mm Hg (5 psig). Gentle agitation is used to minimize the possibility of forming water-in-oil emulsions. Preferably, the fatty acid lower alkyl ester-containing phase is washed with from about 5% to about 20%, by weight, water, more preferably from about 10% to about 15%, by weight. The residence time for the water washing phase preferably ranges from about 5 minutes to about 30 minutes, more preferably from about 5 to about 15 minutes.

Minimizing still bottoms will help to maximize fatty acid lower alkyl ester yields during distillation. Still bottoms can be minimized by minimizing foaming in the stillpot, and by minimizing formation of glycerides and unsaponifiables in the stillpot. Foaming is minimized by washing soap out of the ester to a level below about 1000 ppm, preferably below about 500 ppm, more preferably below about 300 ppm. Glyceride formation is minimized by washing glycerine out of the ester to a level below about 1000 ppm, preferably below about 500 ppm, more preferably below about 300 ppm. Unsaponifiables are minimized by washing basic catalyst out of the ester to a level below about 100 ppm. Still bottoms from one batch can be recycled into the ester-synthesis reaction of a subsequent batch.

The water phase is separated from the ester phase by conventional means (e.g. gravity or centrifugal force). Gravity settling may require up to about 2 hours. A preferred embodiment uses centrifugation of less than about 15 minutes, preferably less than about 10 minutes, and most preferably less than about 5 minutes.

The water-washed fatty acid lower alkyl esters are subjected to fractional distillation; batch (single stage or multi-stage) or continuous distillation may be used. For batch distillation, residence times typically range from about 4 hours to about 30 hours, preferably from about 6 to about 18 hours, more preferably from about 8 to about 12 hours. For continuous distillation, residence times typically range from 0.1 to about 10 minutes, more typically from about 0.5 to about 5 minutes. Pressures from about 0.005 to about 30 mm mercury, preferably from about 1 to about 5 mm mercury, are used in the distillation process.

It is a feature of this invention that the distillation is performed in a manner which avoids generation of high acid values (i.e. acid values greater that 1.0). The high acid value is the result of a high temperature decomposition reaction that can occur with glycerides and methyl esters. Distillation can be done at low temperatures, such as from about 163° C. (325° F.) to about 246° C. (475° F.), in the absence of a strong base, or at higher temperatures, such as from about 246° C. (475° F.) to about 277° C. (530° F.), in the presence of a strong base. The addition of the strong base neutralizes most of the fatty acid generated during the higher temperature distillation, as disclosed in Gibson et al., U.S. Pat. No. 4,931,522, incorporated herein by reference. The addition of the strong base allows the use of higher temperatures which expedite the distillation separation. Suitable bases include sodium hydroxide and sodium methoxide. Generally, the minimum amount of base required to neutralize the amount of fatty acid present is used. The amount of base typically ranges from about 0.01% to about 1%, preferably from about 0.1% to about 0.5%, by weight of the lower alkyl ester used.

One embodiment utilizes a two-step distillation at temperatures of from about 246° C. (475° F.) to about 277° C. (530° F.), in the presence of a strong base. A portion of the lower alkyl esters are distilled from the lower alkyl ester-containing phase. The distillation is stopped, and additional strong base is added to neutralize fatty acids in the fatty acid lower alkyl ester-containing phase. The fatty acid lower alkyl ester-containing phase is neutralized to an acid value of less than about 0.2, preferably about 0. The fatty acid alkyl ester-containing phase is subjected to a second distillation to remove an additional portion of the lower alkyl esters. The distilled fatty acid lower alkyl esters preferably have an acid value of less than about 1.0%.

The fractional distillation may be done batch-wise or continuously under vacuum. Temperatures of about 277° C. (530° F.) or less are preferred for batch distillation; batch distillation above about 277° C. (530° F.) is not recommended since large amounts of fatty acids are generated at temperatures above 277° C. (530° F.). Distillation in a column will generally result in maximum separation of glycerides and color-effecting impurities from the lower alkyl esters, but flash distillation without reflux can also be used.

When single stage, continuous distillation is used, heat treatment is generally necessary prior to distillation to convert monoglycerides to di- or triglycerides in order to prevent volatilization of monoglycerides with lower alkyl esters. Suitable temperatures for heat treatment are from about 70° C. (158° F.) to about 120° C. (248° F.), preferably from about 80° C. (176° F.) to about 100° C. (212° F.). No heat treatment is necessary in a multistage continuous distillation process. For batch distillation; heat treatment occurs as part of the heat up and distillation process.

High purity fatty acid lower alkyl esters having a specific fatty acid chain length can be obtained by multistage fractional distillation; for example, C22 fatty acid lower alkyl esters of a purity of from about 86% to 95% by weight can be obtained and used for the synthesis of solid polyol fatty acid polyesters. The high purity C22 lower alkyl esters generally contain about 0.5% to about 4%, preferably from about 0.5% to about 2%, more preferably from about 0.5% to about 1%, of C18 lower alkyl ester. To remove C14–C18 chain lengths from rapeseed methyl esters through fractional distillation, about the first 45% of the ester is distilled at a reflux ratio of at least about 1:1, the next about 15% is distilled at a reflux ratio of at least about 3:1, and the last about 35% is distilled at a reflux ratio of at least 1:1.

Iodine value (IV) is a measure of the degree of unsaturation of fatty acids. The IV of an oil is determined by the number of grams of iodine which will react with the unsaturated carbon-carbon bonds in 100 grams of oil. When rapeseed oil triglyceride is utilized as a fatty acid source, the rapeseed oil triglyceride can be refined, bleached, or hardened to a lower IV, for example to an IV of about 1 to about 4, and deodorized. The oil is then converted to lower alkyl esters, preferably methyl esters, and water-washed at elevated temperatures and elevated pressures.

When rapeseed oil is used to make C22 lower alkyl esters, it is preferably hardened to an iodine value of about 4 or less, more preferably about 2 or less. In one embodiment, when hardened rapeseed oil is employed as a fatty acid source in the present processes, three fractions are removed during fractional distillation of the lower alkyl esters: a predominately C18 fraction; a mixed C18/C20/C22 fraction, and a predominately C22 fraction. Strong base can be added during the distillation process to neutralize any fatty acid that is generated. Unhardened rapeseed oil can also be used, but this typically requires post-hardening of the predominately C22 ester fractions to an IV of from about 1 to about 4, preferably about 2 or less. If unhardened rapeseed oil is used, the predominately C18 ester fraction is highly unsaturated and is suitable for use in making liquid polyol fatty acid polyesters.

Other oil sources, such as C22 fatty acids or glyceride made from C22 fatty acids, can also be used to make C22 esters. When the lower alkyl ester product is employed in the manufacture of polyol fatty acid polyester, it is preferred that the purity of the C22 fractions is from about 86% to about 95% by weight C22 lower alkyl ester. Distillation can be conducted at low temperatures, such as from about 163° C. (325° F.) to about 246° C. (475° F.), in the absence of a strong base, or at higher temperatures, such as from about 246° C. (475° F.) to about 277° C. (530° F.), in the presence of a strong base. The high C22 lower alkyl ester fraction can be distilled on a column with reflux, or flash distilled without reflux. To achieve a low acid value (low free fatty acid level), the distillation temperature is preferably less than about 274° C. (525° F.), more preferably less than about 246° C. (475° F.), most preferably less than about 218° C. (425° F.). The total batch residence time is preferably less than about 20 hours, more preferably less than about 10 hours, most preferably less than about 1 hour.

It is desirable for the fatty acid lower alkyl esters to have a colorless visual appearance. Preferably the ester color is about 0.5 or less Lovibond yellow, more preferably about 0.2 or less, most preferably 0.0. Color in fatty acid lower alkyl esters can come from a preponderance of carbon-carbon and carbon-oxygen double bonds in the ester, and from minor components such as pigments and polymerized esters.

The presence of double bonds in the ester can be minimized by using low IV oil, preferred is low IV rapeseed oil. Avoiding exposure to heat, light, trace metals and air during processing of the oil and ester will minimize double bond formation. Two measures of oxidation commonly used in the processing of oil and lower alkyl esters are peroxide value and carbonyl value. Preferably, the peroxide value is kept below about 2 mcq/kg, more preferably below about 1 mcq/kg, during oil and ester processing. Preferably, the carbonyl value is kept below about 200 ppm, more preferably below about 100 ppm, and most preferably below about 50 ppm, in the ester processing.

Low carbonyl content can be achieved by pretreating the alkyl esters prior to reaction with the polyol. The alkyl esters are distilled in the presence of a strong base, preferably an alkoxide base. Low carbonyl fatty acid lower alkyl esters are separated from the initial distillate (top cut) and still bottoms, both of which are high in carbonyl groups, for example as described by Gibson, et al., U.S. Pat. No. 4,931,552, which is incorporated herein by reference. Since carbonyl content can increase in the presence of oxygen, it is desirable to minimize subsequent atmospheric oxidation by promptly cooling the alkyl esters after distillation and by storing the alkyl esters in closed containers, preferably under nitrogen.

Although single stage distillation can be used, multistage distillation is preferred as multistage distillation effectively separates higher molecular weight minor components from the alkyl ester. Such minor components include chlorophyll, carotenoids, and polymers. Preferably short-path distillation equipment is not used, as it is more likely to result in entrainment or flashing of minor components into the distillate products.

Behenic acid methyl esters, or C22 methyl esters, are preferred fatty acid lower alkyl esters. Such C22 methyl esters are preferred for the synthesis of solid polyol fatty acid polyesters, particularly for the synthesis of solid sucrose fatty acid polyesters. High purity C22 methyl esters according to the invention have a purity of at least about 86% C22. The behenic acid methyl esters have an IV of preferably about 4 or less, more preferably about 2 or less; and are visually colorless, with a Lovibond yellow of preferably about 0.5 or less, more preferably 0.2 or less, most preferably 0.0.

The behenic acid methyl esters have an acid value of generally less than about 1.0, preferably less than about 0.5, more preferably less than about 0.3, and most preferably less than about 0.2. A low acid value (low free fatty acid level) is desirable in the synthesis of polyol fatty acid polyester since the free fatty acid neutralizes the basic catalyst, thereby slowing the reaction. For example, at a catalyst level of 0.06 moles catalyst/moles sucrose, the time required to convert sucrose and C22 methyl ester containing 0.55% fatty acid to 75% octaester is 15 hours in a stirred tank reactor under vacuum. However, when the C22 methyl ester contains only 0.15% fatty acid, 0.03 moles catalyst/moles sucrose is capable of catalyzing the reaction in 8.5 hours.

The colorless high purity fatty acid alkyl esters produced according to the inventive methods can be used to form polyol fatty acid polyesters. Generally, the polyol fatty acid polyesters so produced require less bleaching than polyol polyesters made with lower alkyl esters of lesser purity. Additionally, the low levels of glycerine and glycerides in the high purity fatty acid alkyl esters assure that the polyol fatty acid polyester product will have few, if any, calories. As used herein, the term "polyol fatty acid polyesters" is intended to include fatty acid esters of polyols in which the polyol hydroxyl groups are replaced with esters of fatty acids. Preferred polyol fatty acid polyesters are sucrose polyesters having on average at least five ester linkages per molecule sucrose, in which the fatty acid chains have from about eight to about twenty-four carbon atoms.

As used herein, the term "polyol" is intended to include any aliphatic or aromatic compound containing at least two free hydroxyl groups. Suitable polyols can be selected from the following classes: saturated and unsaturated straight and branch chain linear aliphatics; saturated and unsaturated cyclic aliphatics, including heterocyclic aliphatics; or mononuclear or polynuclear aromatics, including heterocyclic aromatics. Carbohydrates and non-toxic glycols are preferred polyols. Monosaccharides suitable for use herein include, for example, mannose, galactose, arabinose, xylose, ribose, apiose, rhamnose, psicose, fructose, sorbose, tagatose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. Natural sugar alcohols which are suitable for use herein are sorbitol, mannitol, and galactitol.

Particularly preferred classes of materials suitable for use herein include the monosaccharides, the disaccharides and sugar alcohols. Preferred unesterified polyols include glucose, fructose, glycerol, polyglycerols, sucrose, zylotol, and sugar ethers. Preferred unesterified polyols also include alkoxylated polyols such as alkoxylated glycerol, alkoxylated polyglycerols, sorbitol alkoxylated glycerines, and alkoxylated polysaccharides, and linked alkoxylated polyols such as linked alkoxylated glycerines.

Suitable alkoxylated polyols are described in U.S. Pat. Nos. 5,288,884; 5,298,637; 5,362,894; 5,387,429; 5,446,843; 5,589,217 and 5,597,605, incorporated herein by reference. Suitable alkoxylated polyols include alkoxylated sugar alcohols, alkoxylated monosaccharides, alkoxylated disaccharides, alkoxylated polysaccharides, alkoxylated $C_2-C_{10}$ aliphatic diols, and alkoxylated $C_3-C_{12}$ aliphatic triols. Preferred alkoxylated $C_3-C_{12}$ aliphatic triols are alkoxylated glycerols, more preferred are propoxylated glycerols, and particularly preferred are propoxylated glycerols having from about 3 to about 21 moles of propylene oxide per mole glycerol. Preferred alkoxylated polysaccharides are alkoxylated polysaccharides containing anhydromonosaccharide units, more preferred are propoxylated polysaccharides containing anhydromonosaccharide units, as described in U.S. Pat. No. 5,273,772, incorporated herein by reference. Preferred linked alkoxylated glycerines include those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544. A particularly preferred polyol is sucrose.

Suitable fatty acid esters can be derived from either saturated or unsaturated fatty acids. Suitable preferred fatty acids include, for example, capric, lauric, palmitic, stearic, behenic, isomyristic, isomargaric, myristic, caprylic, and anteisoarachadic. Suitable preferred unsaturated fatty acids include, for example, maleic, linoleic, licanic, oleic, linolenic, erythrogenic acids. In a preferred embodiment of the invention, the fatty acid chains have from about two to about twenty-four carbon atoms. Hydrogenated or unhydrogenated lower alkyl esters obtained from fish oil, soybean oil, palm kernel oil, coconut oil, sunflower oil, safflower oil, corn oil, canola oil, and high erucic acid rapeseed oil are preferred. More specifically, C22 fatty acid lower alkyl esters are preferred for synthesis of solid polyol fatty acid polyesters, with C22 fatty acid methyl esters being particularly preferred. Rapeseed oil is a preferred source of C22 fatty acids. Additionally, C16–C18 fatty acid lower alkyl esters are preferred for synthesis of liquid polyol fatty acid polyesters, with C18 fatty acid methyl esters being particularly preferred. Tallow, soybean oil and cottonseed oil are preferred sources of C16–C18 fatty acids. Bleaching and deodorizing of vegetable oil prior to lower alkyl ester synthesis can optionally be employed. The oil can also be alkali refined.

As set forth above, the high purity lower alkyl esters synthesized according to this invention are advantageous for use in polyol fatty acid polyester synthesis methods which utilize lower alkyl esters. Such processes are disclosed in U.S. Pat. Nos. 3,963,699; 4,517,360; 4,518,772; 4,806,632 and 5,491,226, and co-pending applications Schafermeyer, et al., Ser. No. 08/689,119, and Corrigan et al., Ser. No. 08/683,899, all of which are incorporated herein by reference. Preferably the lower alkyl esters will be methyl esters. Methyl esters made according to the invention generally have a level of monoglyceride below about 500 ppm, a non-detectable level of di- and triglyceride, and a glycerine level of less than about 200 ppm. Minimal level of glycerine present in the methyl ester prior to the distillation minimizes the amount of residue during the distillation to less than 10%, preferably less than 5%. Polyol fatty acid polyester synthesized using methyl esters according to the present invention generally have less than about 0.5%, preferably less than about 0.2%, more preferably less than about 0.1%, by weight, triglyceride.

A suitable polyol fatty acid polyester synthesis process is a solvent-free transesterification reaction. In the first step of the transesterification synthesis process, polyol, fatty acid lower alkyl ester, basic reaction catalyst, and optionally a soap are combined to form a heterogeneous mixture. In general, the heterogeneous mixture comprises from about 5% to about 25%, preferably from about 10% to about 20%, by weight of the polyol; from about 70% to about 92%, preferably from about 75% to about 85%, by weight of the fatty acid esters; from about 1% to about 30%, preferably from about 2% to about 10%, by weight of an alkali metal fatty acid soap; and from about 0.01% to about 5%, preferably from about 0.01% to about 0.5%, more preferably from about 0.05% to about 0.3%, by weight of the basic catalyst.

Suitable basic catalysts for the polyol transesterification include alkali metals such as sodium, lithium and potassium; alloys of two or more alkali metals such as sodium-lithium and sodium-potassium alloys; alkali metal hydrides, such as sodium, lithium and potassium hydride; alkali metal lower ($C_1$–$C_4$) alkyls such as butyl-lithium; and alkali metal alkoxides of lower ($C_1$–$C_4$) alcohols, such as lithium methoxide, potassium t-butoxide, potassium methoxide, and/or sodium methoxide. Other suitable basic compounds include carbonates and bicarbonates of alkali metals and alkaline earth metals. A preferred class of basic catalysts include potassium carbonate, sodium carbonate, barium carbonate, or mixtures of these compounds having particle sizes that are less than about 100 microns, preferably less than about 50 microns. It has been found that when these specific compounds are used as catalysts, increased yields of light-colored higher polyol polyesters are obtained when compared to essentially identical reactions carried out using more conventional catalysts, such as sodium hydride, potassium hydride, soap, or sodium methoxide. These preferred catalysts can be used in admixture with the more conventional basic catalysts, described above. Potassium carbonate and/or potassium methoxide are preferred catalysts. The use of these catalysts is further disclosed in U.S. Pat. No. 4,517,360 (Volpenhein), which is incorporated herein by reference.

Suitable soaps for the polyol transesterification include alkali metal fatty acids soaps. As used herein, the term "alkali metal fatty acid soaps" is intended to include the alkali metal salts of saturated or unsaturated fatty acids having from about eight to about twenty-four carbon atoms, preferably from about eight to about eighteen carbon atoms. Accordingly, suitable alkali metal fatty acid soaps include, for example, lithium, sodium, potassium, rubidium, and cesium salts of the fatty acids described herein. Mixtures of fatty acids derived from soybean oil, sunflower oil, safflower oil, cottonseed oil, palm oil and corn oil are preferred. Accordingly, preferred alkali metal fatty acid soaps include, for example, the potassium soap made from soybean oil fatty acids.

In forming the polyol fatty acid polyester, the heterogeneous mixture is heated to a temperature of from about 110° C. (230° F.) to about 180° C. (356° F.), preferably from about 127° C. (260° F.) to about 145° C. (293° F.), more preferably from about 132° C. (270° F.) to about 135° C. (275° F.), under pressure from about 0.01 to about 2500 mm, preferably from about 0.01 to about 1500 mm. A homogeneous melt of partially esterified polyol and unreacted starting materials will form in from about one to about four hours. As used herein, the term "partially esterified polyol" are those esters of the polyol wherein up to about 50% of the hydroxy groups of polyol have been esterified. In the case of sucrose, the primary sucrose fatty acid partial esters are mono, di, and/or tri-esters.

In the second step of the transesterification process, an excess of fatty acid lower alkyl ester is added to the homogeneous melt formed in the first step. As used herein, the term "excess" is an amount beyond that required to form fully esterified polyol. When fatty acid methyl esters are used, it is preferred that after the excess esters are added to the reaction mixture, the mixture is heated to a temperature of from about 120° C. (248° F.) to about 160° C. (320° F.), preferably about 135° C. (275° F.), at a pressure from about 0.1 to about 2500 mm, preferably from about 0.5 to about 1500 mm, of mercury. The reaction time for the second step is preferably less than about 10 hours, and generally is from about 2 to about 8 hours. During the second step, the partially esterified polyol is further esterified to provide highly esterified polyol fatty acid polyesters. As used herein, the term "highly esterified polyol fatty acid polyester" refers to a polyol wherein at least about 50%, preferably at least about 70%, and most preferably at least about 96% of the hydroxy groups are esterified. In the case of highly esterified sucrose polyesters, this typically refers to the hexa-, hepta-, and particularly octa-esters.

As the transesterification reaction proceeds, a lower alcohol is formed as a by-product. In order to promote the reaction, the alcohol by-product is preferably removed. Many removal techniques are known in the art which can be used to effectively and efficiently remove the lower alkyl alcohol. Vacuum removal with or without an inert gas (e.g., nitrogen) sparging can be employed. Inert gas sparging, with sub- or super atmospheric conditions, with or without agitation, can be employed.

The use of specific catalysts and soap:polyol ratios permit the combination of the first and second steps into a single reaction step. The use of such catalysts is further disclosed in U.S. Pat. No. 4,517,360 (Volpenhein), and the use of such soap:polyol ratios is further disclosed in U.S. Pat. No. 4,518,772 (Volpenhein), both references incorporated herein by reference. In this single step approach, a mixture of a polyol, alkali metal fatty acid soap, basic catalyst selected from potassium carbonate, sodium carbonate, and barium carbonate, and excess fatty acid lower alkyl ester is heated to a temperature from about 100° C. (212° F.) to about 180° C. (356° F.) at a pressure from about 0.1 to about 760 mm of mercury. The soap:polyol molar ratio is from about 0.1:1 to about 1:1, preferably from about 0.1:1 to about 0.75,1, more preferably from about 0.1:1 to about 0.5:1, most preferably from about 0.1:1 to about 0.25:1.

In the final stage of the transesterification process, the polyol fatty acid polyesters are separated from the reaction mixture containing polyesters, by-products, and unreacted starting materials. Separation can be accomplished with any of the separation procedures routinely used in the art. Distillation, water washing, and conventional refining techniques or solvent extractions are preferred. The unreacted fatty acid lower alkyl esters recovered from the reaction mixture can be recycled, as described in co-pending application, Kenneally et al., Lower Alkyl Ester Recycling in Polyol Fatty Acid Polyester Synthesis, Case 6506, incorporated herein by reference. The polyol fatty acid polyester product obtained will have high levels of functional saturates, low acid values, colorless appearance, and low levels of glycerine and glycerides.

Liquid polyol polyesters may cause passive oil loss from the body; however, solid non-digestible polyol polyesters do not cause passive oil loss. Combining liquid and solid non-digestible polyol polyesters provides non-digestible non-caloric compositions causing reduced or no passive oil loss. It is believed that the combination of such solid polyol polyesters with liquid polyol polyesters provides sufficient viscosity and sufficiently high liquid/solid stability at body temperature to provide passive oil loss control. See Elsen et al., U.S. Pat. No. 5,422,131; Jandacek, U.S. Pat. No. 4,005,195; and Jandacek et al., U.S. Pat. No. 4,005,196, incorporated herein by reference. Solid polyol polyesters made with C22 methyl esters according to the invention are efficient crystallizing agents, i.e., they are efficient at providing a stiffening effect. However, the present invention is not bound to or limited by this theory.

The following examples are intended only to further illustrate the invention and are not intended to limit the scope of the invention which is defined in the claims.

EXAMPLE 1

Methyl ester is synthesized using a glycerol behenate feedstock. The glycerol behenate is a mixture of mono-, di- and triglycerides with an iodine value of 0.5 and a chain length composition of:

| | |
|---|---|
| C16 | 1.0% |
| C18 | 1.3% |
| C20 | 4.2% |
| C22 | 90.9% |
| C24 | 0.9% |
| other | 1.7% |

High purity glycerol behenate (650 grams) is mixed with 117 grams of methanol and 9.1 grams of sodium methylate solution (25% by weight in methanol) in a one-liter reaction flask with agitation at 70° C. (158° F.) for about 1 hour. The agitation is turned off, and the glycerine rich phase is allowed to settle for about 2 hours and is then decanted. Two water washes are performed on the ester-containing phase. For each water wash, 33 grams of hot deionized water is added to the ester-containing phase with agitation for about 5 minutes; the agitation is then turned off, and a water/methanol phase is allowed to settle for about 1 hour and is then decanted.

A batch flash distillation of the ester-containing phase is performed with a one-liter flask, an overhead condenser, a receiver vessel, and a vacuum pump. The ester is heated to a temperature of 440° F. (227° C.) to 480° F. (248° C.) at a pressure of 2 to 7 mm Hg. The total time for distillation is 2 hours. The distillation temperature is moderate and the residence time is low, so base treatment is not necessary during the distillation in order to regulate the acid value. The material balance for the distillation is approximately 94% distilled ester, and 6% still bottoms. The distilled ester is visually clear, has an acid value of 0.14 and has a composition of:

| | |
|---|---|
| C16 | 0.7% |
| C18 | 1.4% |
| C20 | 4.4% |
| C22 | 91.7% |
| C24 | 1.5% |
| other | 0.3% |

EXAMPLE 2

Methyl ester is synthesized using a glyceryl behenate feedstock. The glycerol behenate is a mixture of mono-, di-, and triglycerides with an iodine value of 0.5, and a chain length composition of:

| | |
|---|---|
| C16 | 0.4% |
| C18 | 1.5% |
| C20 | 5.8% |
| C22 | 90.5% |
| C24 | 1.8% |

Glycerol behenate (3816 lbs) is mixed with 630 lbs of methanol and 67 pounds of sodium methylate solution (25% by weight in methanol) in a 750 gallon tank with agitation at 70° C. (158° F.) for about 1 hour. The agitation is turned off, and a glycerine rich phase is allowed to settle and is then decanted. One water wash is performed on the ester-containing phase by adding 1500 lbs of hot (70° C.) deionized water to the ester-containing phase. The mixture is agitated for about 5 minutes; the agitation is then turned off, and a water/methanol phase is allowed to settle and is then decanted. About 1602 lbs of water/methanol phase is removed. The soap level in the ester-containing phase after water-washing is 320 ppm.

A batch fractional distillation of the ester-containing phase is performed using the 750 gallon tank as a stillpot, along with an overhead condenser, a receiver vessel, and a vacuum pump. The ester-containing phase is heated to a temperature of 350° F. (177° C.) to 400° F. (204° C.) at a pressure of 1 mm Hg. The total time for distillation is 18 hours. The distillation temperature is low and the residence time is moderate, so base treatment is not necessary during the distillation.

The material balance for the distillation is approximately 97% distilled ester, and 3% still bottoms. The distilled ester is visually clear, has an acid value of 0.1, and has a composition of:

| | |
|---|---|
| C16 | 0.5% |
| C18 | 1.5% |
| C20 | 6.0% |
| C22 | 90.0% |
| C24 | 2.0% |

EXAMPLE 3

Methyl ester is synthesized using a hardened rapeseed oil feedstock. The rapeseed oil has an iodine value of 1.2 and a chain length composition of:

| | |
|---|---|
| C16 | 3.5% |
| C18 | 38.0% |
| C20 | 9.7% |
| C22 | 47.4% |
| C24 | 1.4% |

Hardened rapeseed oil (42,865 lbs) is mixed with 10,027 lbs of methanol and 508 pounds of sodium methylate solution (25% by weight in methanol) in a 10,000 gallon tank with agitation at 70° C. (158° F.) for about 1 hour. The agitation is turned off, and the glycerine rich phase is allowed to settle and is then decanted. Two water washes are performed on the ester-containing phase. For each water wash, 2280 lbs of hot deionized water is added to the ester-containing phase with agitation for about 5 minutes; the agitation is then turned off, and a water/methanol phase is allowed to settle and is then decanted.

A batch fractional distillation of the ester-containing phase is performed with a stillpot, a packed column with 10 theoretical stages, an overhead condenser, a receiver vessel, and a vacuum pump. The ester-containing phase is heated to a temperature of 450° F. (232° C.) to 525° F. (274° C.) at a pressure of 5 to 25 mm Hg. The total time for distillation is 45 hours. The distillation temperature is high and the residence time is high, so base treatment is necessary during distillation in order to regulate acid value. The following weight percents of fractions are taken:

| | | |
|---|---|---|
| Light Cut | C16–C20 ester, glycerine | 58% |
| Product Cut | primarily C22 methyl ester | 32% |
| Still Bottoms | nonvolatile material | 10% |

The reflux ratio varies from about 1.0 for the first half of the light cut to 3.0 for the latter half of the light cut and back to 1.0 for the product cut. After the light cut is distilled, the acid value of the light cut is 1.0, and the acid value of the material left in the stillpot is 2.2. Dry sodium methylate (112 lbs) is added to the stillpot at a temperature of 300° F. (149° C.) to neutralize the fatty acid to an acid value of 0.04. The product cut is then distilled and collected; the acid value of the product is 0.8. The composition of the product cut is approximately 92.6% C22 and 1.8% C18. The product is visually clear and the levels of residual glycerine and residual monoglyceride are below 150 ppm.

EXAMPLE 4

Solid sucrose fatty acid polyester is made by a batch process. Cottonseed methyl ester having an IV of 90 (302 lbs) is mixed with 1,523 lbs of C22 methyl ester with an IV of 1, 367 lbs of powdered sucrose, 67 lbs of potassium stearate soap, and 2.8 lbs of potassium carbonate catalyst. The reaction is conducted in a 750 gallon reactor with an agitator, an overhead condenser, a receiver vessel, and a vacuum system. The impellers on the agitator are either pitched blade (for solids suspension) or Rushton turbine (for gas dispersion). A four-stage vacuum system capable of pulling 1.0 mm Hg is used to remove methanol by-product from the reactor. Nitrogen sparging is used as a stripping agent to assist in methanol removal.

The first step of the transesterification reaction proceeds for about 5 hours at a temperature of about 275° F. (135° C.) and a pressure of about 1 to about 9 mm Hg. Additional methyl ester (321 lbs of cottonseed methyl ester and 1619 lbs of C22 methyl ester) and potassium carbonate catalyst (2.8 lbs) are then added. The second step of the transesterification reaction proceeds for about 8 hours at a temperature of about 275° F. (135° C.) and a pressure of about 1 to about 9 mm Hg. Generally the total residence time to achieve 75% octaester in a reactor is about 10 to about 14 hours.

The product is then centrifuged to remove soap, water washed to remove color bodies and to chelate trace metals, and bleached with silica gel for final soap and color removal. Centrifugation is performed with a disc stack centrifuge, generally about 95% of the potassium stearate emulsifier is removed from the crude polyol polyester. Water-washing is done in a stirred tank with a pitched blade agitator at a water level of about 18% by weight of the crude polyol polyester and a mixing time of from about 10 to about 30 minutes. The water washing temperature is about 185° F. (85° C.). The water phase is separated by gravity settling. The crude polyol polyester is then dried to a moisture content of less than about 0.1% in a vacuum dryer. Silica gel bleaching is performed by contacting dry silica with the crude polyol polyester in a stirred tank for 30 minutes; the silica level is about 1% by weight of the crude polyol polyester. The silica gel is separated from the polyol polyester in a filter press.

The product is then evaporated and steam stripped to remove excess methyl ester. The evaporation is performed with a wiped film design evaporator, for example operating under a pressure of about 1.0 mm Hg and a temperature of about 475° F. (246° C.). Steam stripping of the polyol polyester completes the methyl ester removal. Steam stripping is performed with a packed column, for example with countercurrent flow of steam and polyol polyester operating under a pressure of about 4.0 mm Hg and a temperature of about 475° F. (246° C.). The refined polyol polyester has a residual methyl ester content of less than about 1000 ppm, and has a bland flavor and odor.

The solid sucrose fatty acid polyester can be blended with liquid sucrose fatty acid polyester at a concentration of about 5.8% by weight to obtain a blended product which meets all requirements for control of passive oil loss from the body without excessive waxy mouth feel.

In another embodiment of the invention, the high purity lower alkyl esters synthesized according to this invention are advantageously used in linked esterified alkoxylated polyol synthesis methods. Such processes are disclosed in U.S. Pat. Nos. 5,374,446, 5,427,815 and 5,516,544, incorporated herein by reference.

Alkoxylated polyols may be prepared by alkoxylation techniques known in the art such as, for example, reacting a polyol with an epoxide in the presence of a catalyst, such as alkali metal. The alkoxylated polyol may be reacted with linking segments to form a linked alkoxylated polyol. Polycarbonyl linking segments may be selected from acid entities including free acid, acid anhydrides, acid esters, acid halides and mixtures thereof. Polyether glycol linking segment may be selected from polyepoxide-functionalized polyether glycols; as used herein "polyepoxide functionalize" means having two or more epoxide functional groups capable of undergoing ring-opening reactions to form ether bonds. Suitable polyepoxide-functionalized polyether glycols include diepoxide functionalized polyether glycol. The linked alkoxylated polyol may be reacted by transesterification with lower alkyl esters to form a linked esterified alkoxylated polyol.

A sutiable process for preparing a linked esterified alkoxylated polyol using high purity lower alkyl esters comprises the steps of converting a source of fatty acids to a product mixture comprising fatty acid lower alkyl esters and by-products; water-washing the product mixture at an elevated temperature and an elevated pressure to remove at least a portion of the by-products from product mixture; fractionally distilling the water-washed product mixture to obtain high purity fatty acid lower alkyl esters having an acid value of no greater than about 1.0; reacting a polyol with an epoxide to form an alkoxylated polyol; reacting the alkoxylated polyol with a linking segment to form a linked alkoxylated polyol; and transesterification of the linked alkoxylated polyol with the high purity fatty acid lower alkyl esters.

Preferred linked esterified alkoxylated polyols are those comprising at least one polyether glycol linking segment, at least two polyol segments each of which is connected to the polyether glycol linking segments either directly or through an unesterified oxyalkylene segment, and at least one fatty acid substituent attached to a polyol segment and selected from fatty acid esters and/or fatty acid esterified oxyalkylene segments, as described in U.S. Pat. No. 5,373,336; those comprising at least one polycarbonyl linking segment, at least two polyol segments each of which is connected to the polycarbonyl linking segments either directly or through an oxyalkylene segment, and at least one fatty acid-esterified oxyalkylene segment attached to a polyol segment, as described in U.S. Pat. No. 5,427,815; or those comprising at least two polycarbonyl linking segments, at least three polyol segments each of which is connected to the polycarbonyl linking segments either directly or through an oxyalkylene segment, and at least one fatty acid-esterified oxyalkylene segment attached to a polyol segment, as described in U.S. Pat. No. 5,516,544. Particularly preferred are linked esterified alkoxylated polyols having a molecular weight greater than 6000 and comprising at least two polycarbonyl linking segment, at least three glyceryl segments and at least one $C_6$–$C_{24}$ fatty acid-esterified oxyalkylene segment attached to a glyceryl segment, as described in U.S. Pat. No. 5,516,544.

Having described the preferred embodiments of the present invention, further adaptions of the process described herein can be accomplished by appropriate modifications by one of ordinary skill in the art without departing from the scope of the present invention. A number of alternatives and modifications have been described herein, and others will be apparent to those skilled in the art. Accordingly, the scope of the present invention should be considered in terms of the following claims, and is understood not to be limited to the details of the processes described in the specification.

What is claimed is:

1. A process for making high purity fatty acid lower alkyl esters, comprising the steps of:
    (a) converting a source of fatty acids to a product mixture comprising fatty acid lower alkyl esters and by-products;
    (b) water-washing the product mixture at a temperature of from about 60° C. to about 93° C. and an elevated pressure to remove at least a portion of the by-products from the product mixture; and
    (c) fractionally distilling the water-washed product mixture to obtain high purity fatty acid lower alkyl esters; and
    wherein at least a portion of the fatty acids have from about 20 to about 24 carbon atoms and further wherein the high purity fatty acid lower alkyl esters have an acid value of no greater than about 1.0.

2. A process according to claim 1, further comprising the step of collecting at least one fraction of high purity fatty acid lower alkyl esters during the step of fractionally distilling.

3. A process according to claim 2 wherein the high purity fatty acid lower alkyl esters have an acid value of less than about 0.5.

4. A process according to claim 1 wherein the step of fractionally distilling is performed at a temperature of from about 163° C. to about 246° C. and in the absence of base.

5. A process according to claim 1 wherein the step of fractionally distilling is performed at a temperature of from about 246° C. to about 277° C. and in the presence of a base.

6. A process according to claim 5 wherein step (c) comprises the steps of:
    (1) fractionally distilling the water-washed product mixture to obtain a first portion of the fatty acid lower alkyl esters;
    (2) neutralizing the remaining water-washed product mixture to an acid value of no more than about 0.2; and
    (3) further fractionally distilling the neutralized water-washed product mixture to obtain a second portion of the fatty acid lower alkyl esters.

7. A process according to claim 1 wherein the source of fatty acids is an oil selected from the group consisting of hydrogenated and unhydrogenated fish oil, hydrogenated and unhydrogenated soybean oil, hydrogenated and unhydrogenated palm kernel oil, hydrogenated and unhydrogenated coconut oil, hydrogenated and unhydrogenated sunflower oil, hydrogenated and unhydrogenated safflower oil, hydrogenated and unhydrogenated corn oil, hydrogenated and unhydrogenated cottonseed oil, hydrogenated and unhydrogenated peanut oil, hydrogenated and unhydrogenated canola oil, hydrogenated and unhydrogenated high erucic acid rapeseed oil, and mixtures thereof.

8. A process according to claim 7 further comprising the step of subjecting the oil to at least one step selected from the group consisting of bleaching, deodorizing, hardening and alkali refining, before its conversion.

9. A process according to claim 1 further comprising the step of hardening the fatty acid lower alkyl ester.

10. A process according to claim 1 wherein the water-washed product mixture comprises no more than about 1000 ppm soap, no more than about 1000 ppm glycerides, and no more than about 100 ppm basic catalyst.

11. A process according to claim 2 wherein the fatty acid lower alkyl esters comprise behenic methyl ester.

12. A process according to claim 11 wherein the color of the behenic acid methyl ester is about 0.5 or less Lovibond yellow.

13. A process according to claim 1 wherein the water-washing elevated temperature is from about 77° C. to about 93° C. and the water-washing elevated pressure is from about 760 mm Hg to about 1000 mm Hg.

14. A process for making high purity fatty acid lower alkyl esters, comprising the steps of:
  (a) converting a source of fatty acid to a product mixture comprising fatty acid lower alkyl esters and by-products;
  (b) water-washing the product mixture at a temperature of from about 60° C. to about 93° C. and an elevated pressure to remove at least a portion of the by-products from the product mixture; and
  (c) fractionally distilling the water-washed product mixture to obtain high purity fatty acid lower alkyl esters; and
wherein the step of fractionally distilling is selected from the group consisting of fractionally distilling in the absence of base at a temperature of from about 163° C. to about 246° C. and fractionally distilling in the presence of base at a temperature of from about 246° C. to about 277° C., and wherein at least a portion of the fatty acids have at least about 16 carbon atoms and further wherein the high purity fatty acid lower alkyl esters have an acid value of no greater than about 1.0.

15. A process according to claim 14 wherein the fatty acid lower alkyl esters comprise C18 methyl esters, C20 methyl esters and C22 methyl esters; and the process step (c) comprises the steps of collecting a first fraction comprising C18 methyl esters; collecting a second fraction comprising C18 methyl esters, C20 methyl esters and C22 methyl esters; and collecting a third fraction comprising C22 methyl esters.

16. A process according to claim 15 wherein the third fraction comprises from about 86% to about 95%, by weight, C22 methyl ester.

17. A process according to claim 16 wherein the fatty acid source is behenic acid glycerol ester and the fatty acid lower alkyl esters comprise behenic acid methyl ester; and wherein the color of the behenic acid methyl ester is about 0.5 or less Lovibond yellow.

18. A process for preparing fatty acid polyol polyester comprising the steps of:
  (a) preparing high purity fatty acid lower alkyl esters by
    (1) reacting a fatty acid glycerol ester with a lower alkyl alcohol in the presence of a catalyst to produce a product mixture of fatty acid lower alkyl ester, fatty acid glycerol ester and glycerol;
    (2) separating the product mixture into a glycerol-containing phase and a fatty acid lower alkyl ester-containing phase;
    (3) water-washing the fatty acid lower alkyl ester-containing phase at a temperature of from about 60° C. to about 93° C. and an elevated pressure to remove at least a portion of by-products from the fatty acid lower alkyl ester-containing phase;
    (4) fractionally distilling the resulting water-washed fatty acid lower alkyl ester; and
    (5) collecting at least one fraction of highly purified fatty acid lower alkyl ester; and
  (b) transesterifying the highly purified fatty acid lower alkyl ester of the collected fraction with a polyol to obtain a fatty acid polyol polyester; and
wherein the high purity fatty acid lower alkyl esters have an acid value of less than about 1.0.

19. A process according to claim 18 wherein the lower alkyl alcohol is methanol and the fatty acid glycerol ester is behenic acid glycerol ester.

20. A process according to claim 19 wherein the polyol polyester has a triglyceride level of less than about 0.5%, by weight.

21. A process for preparing a linked esterified alkoxylated polyol comprising the steps of:
  (a) converting a source of fatty acids to a product mixture comprising fatty acid lower alkyl esters and by-products;
  (b) water-washing the product mixture at a temperature of from about 60° C. to about 93° C. and an elevated pressure to remove at least a portion of the by-products from the product mixture;
  (c) fractionally distilling the water-washed product mixture to obtain high purity fatty acid lower alkyl esters having an acid value of no greater than about 1.0;
  (d) reacting a polyol with an epoxide to form an alkoxylated polyol;
  (e) reacting the alkoxylated polyol with a linking segment to form a linked alkoxylated polyol; and
  (f) transesterification of the linked alkoxylated polyol with the high purity fatty acid lower alkyl esters.

22. A process for making high purity fatty acid lower alkyl esters, comprising the steps of:
  (a) converting a source of fatty acids to a product mixture comprising fatty acid lower alkyl esters and by-products;
  (b) water-washing the product mixture at a temperature of from about 77° C. to about 93° C. and an elevated pressure to remove at least a portion of the by-products from the product mixture; and
  (c) fractionally distilling the water-washed product mixture to obtain high purity fatty acid lower alkyl esters; and
wherein at least a portion of the fatty acids have from about 20 to about 24 carbon atoms and further wherein the high purity fatty acid lower alkyl esters have an acid value of no greater than about 1.0.

23. A process according to claim 22 wherein the step of fractionally distilling is performed at a temperature of from about 163° C. to about 246° C. and in the absence of base.

24. A process according to claim 22 wherein the step of fractionally distilling is performed at a temperature of from about 246° C. to about 277° C. and in the presence of a base.

25. A process according to claim 24 wherein step (c) comprises the steps of:
  (1) fractionally distilling the water-washed product mixture to obtain a first portion of the fatty acid lower alkyl esters;
  (2) neutralizing the remaining water-washed product mixture to an acid value of no more than about 0.2; and
  (3) further fractionally distilling the neutralized water-washed product mixture to obtain a second portion of the fatty acid lower alkyl esters.

26. A process according to claim 22 further comprising the step of hardening the fatty acid lower alkyl ester.

27. A process according to claim 22 wherein the fatty acid lower alkyl esters comprise behenic methyl ester.

28. A process according to claim 27 wherein the color of the behenic acid methyl ester is about 0.5 or less Lovibond yellow.

29. A process according to claim 22 wherein the water-washing elevated temperature is from about 88° C. to about 93° C. and the water-washing elevated pressure is from about 760 mm Hg to about 1000 mm Hg.

* * * * *